United States Patent [19]

Yvin et al.

[11] Patent Number: 5,750,472
[45] Date of Patent: May 12, 1998

[54] LAMINARIN AS A SEED GERMINATION AND PLANT GROWTH ACCELERATOR

[75] Inventors: Jean-Claude Yvin; Florence Levasseur, both of Saint Malo; Cyrille Amin-Gendy, Argenteuil; Kiem-Ngoc Tran Thanh, Gif sur Yvette; Pascale Patier, Tassin-la-Deth-Lune; Cyrille Rochas, La Combe de Lancey; Yvette Janine Lienart, St Nizier d'Uriage; Bernard Cloarec, Saint Pol de Leon, all of France

[73] Assignee: Laboratoires Goemar S.A., Saint Malo, France

[21] Appl. No.: 367,130

[22] PCT Filed: Jul. 6, 1993

[86] PCT No.: PCT/FR93/00698

§ 371 Date: Mar. 14, 1995

§ 102(e) Date: Mar. 14, 1995

[87] PCT Pub. No.: WO94/00993

PCT Pub. Date: Jan. 20, 1994

[30] Foreign Application Priority Data

Jul. 7, 1992 [FR] France ................... 92 08387

[51] Int. Cl.⁶ .................................. A01N 43/16
[52] U.S. Cl. .................................. 504/292
[58] Field of Search .................................. 504/292

[56] References Cited

U.S. PATENT DOCUMENTS 4,023,734 5/1977 Herve et al. ............... 241/17
4,125,392 11/1978 Primo ............... 71/3

FOREIGN PATENT DOCUMENTS

| 0 218 770 | 4/1987 | European Pat. Off. |
| 0 538 091 | 4/1993 | European Pat. Off. |
| 3 735 365 | 4/1988 | Germany. |
| 58 144 309 | 8/1983 | Japan. |
| 62-265 208 | 11/1987 | Japan. |
| 3 034 905 | 2/1991 | Japan. |

OTHER PUBLICATIONS

"Beta–(1,3) Glucanase Activity and Quantity of Fungus in Relation to Fusarium Wilt in Resistant and Susceptible Near–Isogenic Lines of Muskmelon", by D. Netzer et al. Physiol Plant Pathol, vol. 14, No. 1, 1979, pp. 47–56.(Biological Abstracts, vol. 68, No. 1, 1979, abstract No. 5199).

"Induction, Purification and Possible Function of Chitinase in Cultured Carrot Cells", by F. Kurosaki et al, Physiol Mol Plant Pathol, vol. 31, No. 2, 1987, pp. 201–210. (Biological Abstracts, vol. 85, No. 2, Jan. 15, 1988, abstract No. 20313).

(List continued on next page.)

*Primary Examiner*—S. Mark Clardy
*Attorney, Agent, or Firm*—Lowe, Price, LeBlanc & Becker

[57] ABSTRACT

The present invention relates to the use of laminarin as a seed germination and plant growth accelerator.

The invention applies to the field of agriculture for treatments via the leaves or to the soil.

19 Claims, 1 Drawing Sheet

OTHER PUBLICATIONS

"Elicitor–Induced Accumulation of Glyceollin and Callose in Soybean Roots and Localized Resistance Against Phytophora Megasperma F. SP. Glycinea", by A. Bonhoff et al, Plant Sci, vol. 54, No. 3, 1988, pp. 203–210. (Biological Abstracts, vol. 86, No. 4, 1998, abstract No. 41880).

"Chitin and Related Compounds as Elicitors of the Lignification Response in Wounded Wheat", by R.B. Pearce et al, Physiol Plant Pathol, vol. 20, No. 1, 1982, pp. 119–124. (Biological Abstracts, vol. 74, No. 8, 1982, abstract No. 56641).

"Enzymic Degradation of the Endosperm Cell Walls of Germinated Sorghum", by G.H. Palmer, World J. Microbiol Biotechnol, vol. 7, No. 1, 1991, pp. 17–21. (Biological abstracts, vol. 91, abstract No. 123505).

"Carbohydrate–Degrading Enzymes in Germinating Wheat", by A.M. Corder et al, Cereal Chem, vol. 66, No. 5, 1989, pp. 435–439. (Biological Abstracts, vol. 89, abstract No. 510384).

"Effect of Carbohydrates in Seaweed Fertilizers", by G. Blunden et al, Proc. Int. Seaweed Symp., 6th Meeting Date 1968; 1969, pp. 647–653. (Chemical Abstracts, vol. 74, No. 5, abstract No. 22224f).

"Induction and Secretion of Alpha Amylase 1–3 1–4–Beta Glucanase and 1–3–Beta Glucanase Activities in Gibberellic Acid and Calcium Dichloride–Treated Half Seeds and Aleurones of Wheat", by A.M. Bernier et al, Cereal Chem, vol. 70, No. 2, 1993, pp. 127–132. (Biological Abstracts, vol. 95, abstract No. 115659).

"Manufacture of Algal Chemicals. III. Laboratory–Scale Isolation of Laminarin from Brown Marine Algae", Black et al., J. appl. Chem., I, Nov. 1951, pp. 505–517.

"Pharmacological Activities of Marine Algae", Güven et al., *Introduction to Applied Phycology*, Editor I. Akatsuka, SPB Academic Publishing, 1990, pp. 67–92.

Bonhoff et al. "Elicitor–Induced Accumulation of Glyceollin . . . " *Plant Science* 54:203–209. 1988.

Bernier et al. "Induction and Secretion of α–Amylase . . . " *Cereal Chemistry* 70(2):127–132. Feb. 1993.

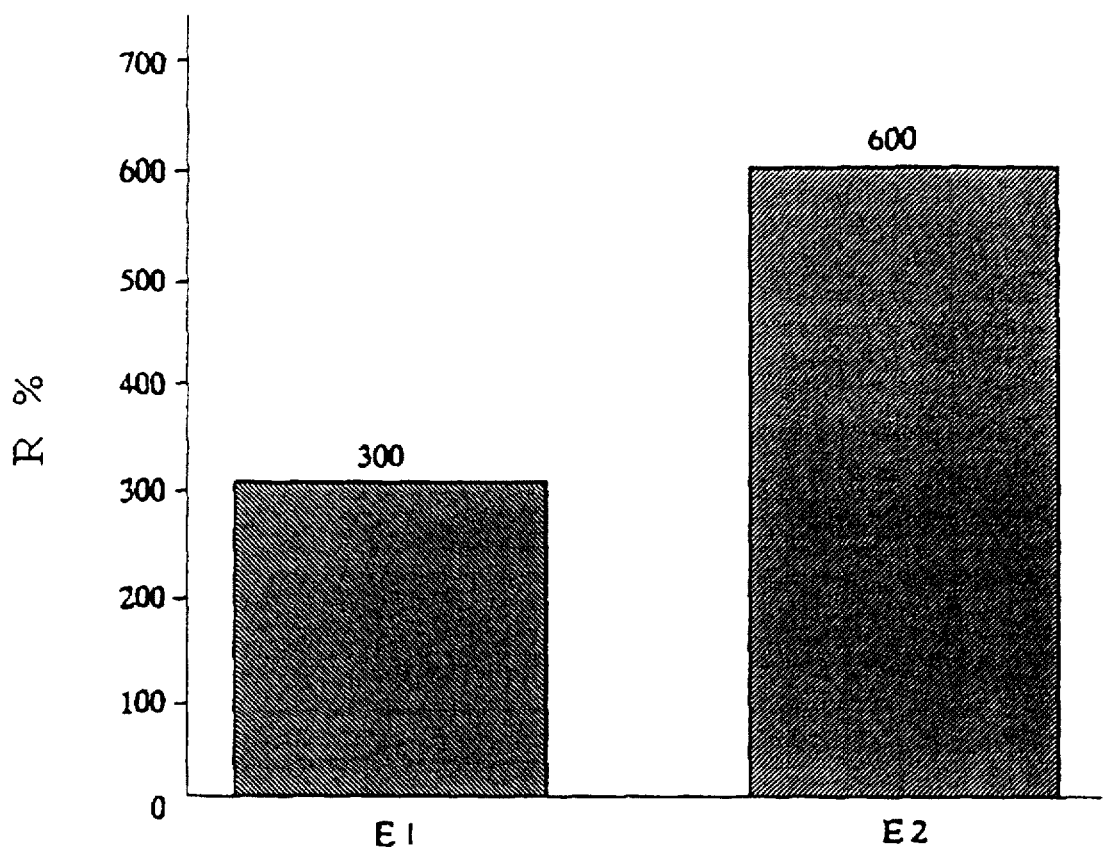

LAMINARIN AS A SEED GERMINATION AND PLANT GROWTH ACCELERATOR

This application has been filed under 35 USC 371 from international application PCT/FR93/00698, filed Jul. 6, 1993.

The present invention relates to the use of laminarin as a seed germination and plant growth accelerator.

It is known that laminarin is a storage polymer of brown algae and consists of polysaccharides whose structures differ slightly according to the nature of the alga.

In general terms, laminarin consists of 20 to 60 D-glucopyranoside units distributed in a main linear chain, in which these units are joined by $\beta(1-3)$ linkages, and branches joined to this main chain by $\beta(1-6)$ linkages.

Some of these chains have a reducing terminal unit consisting of a mannitol unit. The existence of mannose units within this structure is also noted.

Laminarin is generally extracted from brown algae of the Pheophyceae type, and in particular the Fucales or the Laminariales.

Various extraction methods can be used to obtain the laminarin.

Reference may be made for example to the method described by Black et al., Appl. Chem. (1951), volume 1, pages 505 to 517.

More generally, laminarin can be obtained from brown algae by any extraction process which enables the constituents other than laminarin (wall polysaccharides, salts, etc.) to be successively removed.

In particular, these processes use steps involving grinding, precipitation in an acid or basic medium, ultrafiltration and dialysis.

Laminarin is also marketed, for example by Sigma Chimie SARL.

It is further known that sulfated laminarin possesses valuable pharmacological properties, in particular anticoagulant and hypocholesterolemic properties (K. C. Guven et al., Introduction to Applied Physiology, 1990, pages 67 to 92).

Various scientific publications describe the eliciting properties of laminarin, suggesting its use for enhancing plant defense reactions.

Thus NETZER et al. reveal that an infection with the pathogen S. oxysporum triggers the induction of laminarinase (Biological abstracts, vol. 68, no. 1, 1979).

Likewise, BONHOFF et al. reveal the properties of laminarin as an elicitor of phytoalexin and callose (Biological abstracts, vol. 86, no. 4, 1988).

Furthermore, KUROSAKI et al. (Biological abstracts, vol. 85, no. 2, 1988) and PEARCE (Biological abstracts, vol. 74, no. 8, 1982) confirm the eliciting effects of laminarin, in particular in respect of lignification, while at the same time stating that these effects are weak compared with those of the known elicitors.

This state of the art might suggest to those skilled in the art that they use laminarin to enhance plant defense reactions.

It has been discovered, and this is the basis of the invention, that laminarin has the properties of an alpha-amylase elicitor, causing an accelerating action on seed germination and plant growth.

It is pointed out that elicitation is a process which is based on a phase in which a metabolite is recognized by the plant cell and a phase in which a physiological response is generated by a signal. The elicitor therefore corresponds to any signal capable of inducing in plants reactions which enable it to adapt to its environment.

It has been discovered, quite unexpectedly, that laminarin induces the activation of marker enzymes of the growth process in plants, and the stimulation of the proteolytic activity of the treated cells.

It has thus been demonstrated that laminarin and compositions in which it is present increase the production yield of agricultural products by exerting an accelerating action on plant growth, cell elongation and seed germination.

Thus the present invention relates to the use of laminarin as a seed germination and plant growth accelerator.

According to one particular characteristic of this use according to the invention, the laminarin is applied via the leaves or to the soil.

According to another particular characteristic of the invention, this use comprises the preparation of a composition containing an effective amount of laminarin, optionally incorporated with an agriculturally acceptable carrier or vehicle.

According to one particular characteristic, this composition is presented in solid form, especially in the form of powders or granules, or in liquid form, especially in the form of aqueous solutions.

According to another particular characteristic, this composition also contains at least one additional substance selected from deficiency-correcting elements, fungicides, insecticides, herbicides, growth hormones, lipoamino acids and betaines.

Examples of herbicides which can be used are compounds belonging to the group comprising carbamates, cyclohexadiones, sulfonylureas, triazines or uracils.

Examples of fungicides which can be used are compounds belonging to the group comprising dithiocarbamates, hydantoins, imidazoles or triazoles.

Advantageously, this composition contains from 0.005 to 503 by weight of laminarin and preferably from 1 to 253 by weight when it is in solid form, and from 0.005 to 103 by weight of laminarin and preferably from 0.5 to 53 by weight when it is in liquid form.

In general terms, the compositions consistent with the use according to the invention are prepared by mixing laminarin, extracted in powder form, with customary additives, for example solid fillers and/or solvents. Surface-active substances, dispersants or emulsifiers will also be used.

Examples of solid fillers which can be used for the preparation of wettable powders or granules are finely divided kaolin or clay.

When presented in liquid form, these compositions will preferably be obtained by diluting the laminarin in water.

It is also possible to envisage the preparation of spraying compositions based on oil or emulsifiable concentrate, especially in the case of a mixture with additional substances which are insoluble in water.

Examples of plants which can be treated successfully with laminarin within the framework of the use according to the invention are:

fruit crops such as apple trees, pear trees and vines;

cereals such as wheat, maize and rice;

oleaginous plants such as soya, sunflower and colza;

vegetables such as carrots, tomatoes, cauliflowers and potatoes.

In general, laminarin must be used in doses of between 0.005 g and 100 g per liter for treating the leaves, and of between 1 g and 100 g per 100 kg for treating the seeds.

BRIEF DESCRIPTION OF THE DRAWING

The drawing graphically represents the results obtained by enzymatic activation (R) defined as the ratio of the activity measured in elicited cells or protoplasts to the activity measured in untreated cells or protoplasts. E1 and E2 designate the elicitors tested. Each value plotted on the graph results from the processing of pre-experimental data obtained in the course of an elicitation experiment. E1 induces an alpha-amylase activation R of 300% in the cells, whereas laminarin-based composition E2 induces an alpha-amylase activation R of 600%.

The present invention will be illustrated with the aid of the following non-limiting Examples:

First of all, Examples 1 and 2 will give two processes for the extraction of laminarin from a brown alga.

The NMR spectra of the extracts obtained by carrying out the processes described in Examples 1 and 2 contain the characteristic peaks of a commercial laminarin.

EXAMPLE 1

Process for the Extraction of Laminarin from a Brown Alga 300 g of fresh algae of the *Laminaria saccharina* type, harvested in August, are subjected to cryocomminution (−40° C.) by the process described in French patent no. 74 35162.

The product thus obtained has a mean particle diameter of between 50 and 100 μm and a solids content of 10–124%. 0.9 l of 0.34 sulfuric acid is added gradually to 300 g of this product. Extraction is performed in a water bath at a temperature of about 80° C. for 1 hour, with stirring.

This operation is repeated twice.

After neutralization, the extract obtained is treated with polyvinylpyrrolidone in a dose of about 14 by weight. This is done by introducing 9 g of polyvinylpyrrolidone (PVP) into a volume of 90 ml of extract. The PVP is left to thicken for about 2 hours. The resulting solution is added to about 0.9 l of extract, the mixture being stirred for 30 min and then filtered under vacuum on a Whatman GF/A filter.

The liquid obtained in this way is subjected to tangential ultrafiltration on a carbon-ceramic tubular membrane of the "Carbosep" type with a porosity of 50,000 Daltons. A pressure of 1 bar is maintained on the filtration column during the operation.

This gives a filtrate having a volume of about 0.8 liter and a pH of 5.5. The filtrate is then dialyzed on a cellulose ester membrane of the SPECTRA/Por type with a porosity of 500 or 1000 Daltons. The dialyzate is then lyophilized to give 7 g of dry powder, corresponding to pure laminarin.

EXAMPLE 2

Alternative Process for the Extraction of Laminarin from a Brown Alga 300 g of fresh algae of the *Ascophyllum nodosum* type are ground in a knife mill of trademark STEFAN, type VCM5. The resulting product has a particle diameter of less than 1 mm and a solids content of 10–12%. 0.9 l of a 2% aqueous solution of calcium chloride is added to 300 g of this product, precipitating the alginates in particular.

The first extraction is performed in a water bath at a temperature of about 60° C. for 7 hours, with stirring. The first extract is then recovered by filtration and the 300 g of ground product are extracted a second time in 0.9 l of a 25 aqueous solution of calcium chloride under the same conditions as the first extraction, i.e. in a water bath at a temperature of about 60° C., but this time overnight, with stirring. Then the second extract is also recovered by filtration.

The two extracts obtained in this way are then combined and subjected to diafiltration to remove the mineral salts.

This was done using a Pellicon system marketed by Millipore, equipped with a cassette of porosity 1000 Daltons and associated with a Procon pump, also marketed by Millipore.

The decrease in the ion content of the extract is followed by regular measurement of the resistivity.

The diafiltration is continued until the resistivity of the residue is about 1000 Ohms.cm.

The residue is then treated on a column of anion exchange resin of the strong exchanger type, such as Amberlite IRA 400, or of the weak exchanger type, such as AMBERLITE IR 45.

Two techniques can be used:

either a batch process: After regeneration with sodium hydroxide and rinsing with demineralized water, the resin is placed directly in a vessel containing the residue. The mixture is stirred for 1 hour and decanted and the filtrate is recovered.

or column chromatography: After regeneration with sodium hydroxide and rinsing with demineralized water, the resin is introduced into a glass column of diameter 2–3 cm to a height of 20 cm. The filtrate is then deposited on the top of the column and caused to penetrate slowly into the resin. The column is then rinsed with demineralized water.

The eluate is then dialyzed on a cellulose ester membrane of the Spectra/Por type with a porosity of 500 or 1000 Daltons. The dialyzate is then lyophilized to give 7 g of dry powder, corresponding to pure laminarin.

EXAMPLE 3

Demonstration of the Properties of Laminarin

The properties of laminarin and compositions in which it is present were demonstrated by performing the following experiments:

Experiment No. 1

Seed Germination Test

The influence of laminarin on seed germination was evaluated using the following protocol:

Without prior soaking, carrot, lettuce and endive seeds are germinated in batches of 10 in Petri dishes of diameter 5 cm:

in an aqueous solution (control batch), in a solution containing growth substances (kinetin or indolacetic acid (IAA) at concentrations of $10^{-6}M$), and in a solution containing laminarin at different concentrations.

The Petri dishes are placed in an enclosure at 25° C. in the dark.

The results obtained after 10 days are collated in the following Table:

| PRODUCT TESTED | % GERMINATION | | |
|---|---|---|---|
| | carrot | lettuce | endive |
| Water | 35 | 11 | 12 |
| IAA $10^{-6}M$ | 30 | 0 | 15 |

-continued

| PRODUCT TESTED | % GERMINATION | | |
|---|---|---|---|
| | carrot | lettuce | endive |
| Kinetin $10^{-6}$M | 27 | 26 | 12 |
| Laminarin 0.1 µg/ml | 25 | 16 | 15 |
| Laminarin 0.2 µg/ml | 34 | 20 | 13 |
| Laminarin 0.4 µg/ml | 47 | 24 | 17 |
| Laminarin 0.6 µg/ml | 45 | 34 | 20 |
| Laminarin 0.8 µg/ml | 100 | 33 | 10 |
| Laminarin 1 µg/ml | 27 | 32 | 15 |
| Laminarin 2 µg/ml | 41 | 17 | 12 |
| Laminarin 4 µg/ml | 34 | 26 | 9 |
| Laminarin 6 µg/ml | 24 | 30 | 9 |
| Laminarin 8 µg/ml | 35 | 19 | 24 |
| Laminarin 10 µg/ml | 41 | 26 | 13 |

Therefore, under the experimental conditions tested, laminarin has an optimal activity at concentrations of:

0.8 µg/ml for carrot seeds, 0.6, 0.8 and 1 µg/ml for lettuce seeds, and 0.4, 0.6 and 0.8 µg/ml for endive seeds.

The results thus demonstrate the influence of laminarin on the germination of different types of seeds.

Experiment No. 2

Elongation of Wheat Coleoptiles

Wheat seeds are germinated at 25° C. in the dark.

The coleoptiles reach a length of 2.5 to 3 cm after 3 days. After excision of the coleoptiles, segments 8 mm in length are cut out.

To determine whether the apical zone, which is the center of endogenous production of auxin, will interfere synergistically or antagonistically with the laminarin, two batches were tested, one containing the apical zone and the other not.

For each experiment, two batches of 10 coleoptile fragments are brought into contact with 5 ml of an aqueous solution of the test product (IAA $10^{-6}$M and laminarin at different concentrations) in Petri dishes of diameter 5 cm.

The elongation is measured after 20 hours of incubation in the dark at 25° C.

The results obtained are collated in the following Table:

| TREATMENT | AVERAGE ELONGATION |
|---|---|
| Water | 9 ± 0.87 |
| IAA $10^{-6}$M | 11.12 ± 0.29 |
| Laminarin 0.1 µg/ml | 12 ± 0.33 |
| Laminarin 0.2 µg/ml | 12.85 ± 0.99 |
| Laminarin 0.4 µg/ml | 11 ± 0.53 |
| Laminarin 0.6 µg/ml | 10.33 ± 0.86 |
| Laminarin 0.8 µg/ml | 11.83 ± 1.54 |
| Laminarin 1 µg/ml | 11.16 ± 1.67 |
| Laminarin 2 µg/ml | 11.16 ± 1.67 |
| Laminarin 4 µg/ml | 11.25 ± 1 |
| Laminarin 6 µg/ml | 10.42 ± 0.7 |
| Laminarin 8 µg/ml | 11.14 ± 0.97 |
| Laminarin 10 µg/ml | 11.33 ± 1.07 |

Under the experimental conditions tested, laminarin has an optimal activity at concentrations of 0.1 and 0.2 µg/ml.

Laminarin has a very favorable activity on the elongation of wheat coleoptiles. It therefore acts as a growth regulator.

EXAMPLE 4

Demonstration of the Properties of Laminarin towards Alpha-Amylase

The properties towards alpha-amylase of laminarin and compositions in which it is present were demonstrated by performing the following experiment:

PROTOCOL

Suspensions of cells or protoplasts of Rubus fructicosus, i.e. $2.4.10^6$ cells suspended in 50 ml of sodium citrate buffer, are incubated for 60 minutes at room temperature, with circular stirring at 80 rpm, in the presence or absence of elicitors.

The elicitors tested correspond to the laminarin-containing compositions produced in Examples no. 1 and no. 2, called E1 and E2 respectively.

The concentrations of E1 and E2 used for this elicitation test are 0.1 g of ose per liter.

At the end of the experiment, the cells or protoplasts are recovered by centrifugation (500 g, 5 minutes at 4° C.) and taken up in 50 mM Tris-HCl buffer (pH 7.2) enriched in NaCl (1M). The cells recovered by centrifugation (7300 g, 10 minutes at 4° C.) are washed twice in the presence of sodium citrate buffer, containing neither sucrose nor mannitol, before being taken up in 50 mM Tris-HCl buffer (pH 7.2) enriched in NaCl (1M).

The alpha-amylase activity used to determine the eliciting potential of compositions E1 and E2 is analyzed according to the following protocol:

An enzymatic extract is prepared at +4° C. from the elicited or non-elicited cells. The cells, taken up in 50 mM Tris-HCl buffer (pH 7.2) enriched in NaCl (1M) (1/5 v/v), are ground with a Polytron homogenizer; the sample is kept in crushed ice throughout the operation. The ground product is centrifuged (1200 g, 15 min at 4° C.) and the supernatant is concentrated by ultrafiltration on an Amicon cell equipped with a PM 10 membrane (cut-off threshold 10,000 Daltons), and is then dialyzed against distilled water with the aid of Ultrafrec units (Millipore) (cut-off threshold 10,000 Da).

The alpha-amylase activity is assayed after incubation of the enzymatic extract (10 µg of proteins) at 40° C. for a variable time (1 to 6 hours) in the pre sence of the substrate (50 µg of soluble starch) in 200 µl of 0.1M sodium acetate buffer (pH 5.0) or 0.1M sodium phosphate buffer (pH 7.0). The reaction is stopped by heating at 100° C. for 10 minutes.

The assay of the alpha-amylase activity is based on quantification of the reducing sugars released, by Somogyi's method (1952). The blanks consist of reaction media containing no enzymatic extract or containing extracts heated to 100° C.

The enzymatic activity (A) is expressed in µmol of glucose equivalents released per hour of enzymatic reaction and per mg of proteins.

RESULTS

1. Expression of the Results

The enzymatic activation (R) is defined as the ratio of the activity measured in elicited cells or protoplasts to the activity measured in untreated cells or protoplasts, the activity of the untreated cells or protoplasts being arbitrarily set at 100.

2. Results: Elicitation of Alpha-Amylase Activity

The results obtained have been plotted in FIG. 1.

Each value plotted in this Figure results from the processing of 3 experimental data obtained in the course of an elicitation experiment.

Laminarin-based composition E1 induces an alpha-amylase activation R of 300% in the cells, where as laminarin-based composition E2 induces an alpha-amylase activation R of 600%.

CONCLUSIONS

The results obtained show that the composition produced in Example no. 2 and, to a lesser extent, that produced in Example no. 1 are capable of stimulating an alpha-amylase activity, alpha-amylase being a marker enzyme of the growth process, which is involved especially during initial germination phases.

Laminarin can therefore be used as a seed germination and plant growth accelerator.

Different compositions for agricultural use, containing laminarin produced in Examples 1 and 2, will be given in Examples 5 to 8.

EXAMPLE 5

Composition for Agricultural use in the Form of Liquid Fertilizer Based on Laminarin Produced in Example 1

The laminarin produced in Example 1 can be used in aqueous solution with one or more deficiency-correcting trace elements, for example a molybdenum salt and a manganese salt.

1 g of laminarin is dissolved in 758 g of water and then 215 g of manganese chloride and 26 g of sodium molybdate are added. The mixture is stirred until dissolution is complete.

This gives a composition having a laminarin content of 0.1%, a molybdenum content of 1% by weight and a manganese content of 1% by weight. This composition can be used as a plant growth stimulant and deficiency corrector by spraying the leaves.

EXAMPLE 6

Agricultural Composition Based on Laminarin Produced in Example 2 in Association with a Fungicide 1 g of laminarin is dissolved in 699 g of water.

300 g of the fungicide Manganil 80 marketed by Bourgeois (no. APV 7000073), containing 80% of the active substance maneb, are suspended in this solution.

This suspension, containing 0.1% of laminarin and 24% of maneb, can be used by spraying on to the surface of the leaves in doses of between 0.1 and 50 ml/l.

This composition exerts an accelerating action on plant growth at the same time as fungicidal protection, in particular against vine and tomato mildew.

EXAMPLE 7

Composition Based on Laminarin Produced in Example 1, used as a Seed Coating Product The laminarin produced in Example 1 can be used in aqueous solution for film-coating a seed of the proteaginous pea type (Ascona variety).

The pea seed, which may or may not have received a plant health treatment, is film-coated with a film-coating machine of trademark HEGE, which is based on the principle of spraying the substances at very high speed on to a mass of seeds rotating about an axis; this causes an eccentric displacement, ensuring perfect intimacy between the seed and the film-coating products.

This method is used to prepare a batch of 500 g of pea seeds, film-coated with 4 ml of an aqueous solution of laminarin produced in Example no. 1, having a content of 5% and completed with a dispersant for improving the product/seed contact.

This composition for film-coating seeds thus has an accelerating action on seed germination and plantlet growth.

EXAMPLE 8

Composition Based on Laminarin Produced in Example 2, employed in the Preparation of Tablets for Agricultural Use Laminarin in powder form, produced in Example no. 2, can be used in the preparation of tablets for watering indoor plants or spraying their leaves.

0.5 g of laminarin produced in Example no. 2 is ground and mixed in a mortar with 0.5 g of a dehydrating agent of the kaolin type. The powder obtained is then compressed in a tableting machine of the alternating type, comprising one fixed die and two punches (one upper and one lower) moving in the vertical direction.

The 1 g granule or tablet obtained is then ejected from the machine and can be used by dissolution in water in the watering can or sprayer.

We claim:

1. A method for accelerating a plant's growth comprising a step of applying a composition containing an effective amount of laminarin to the leaves of said plant.

2. A method for accelerating the growth of a plant comprising a preliminary step of determining the effective amount of laminarin that will accelerate the growth of said plant and a further step of applying a composition containing said effective amount of laminarin to the leaves of said plant.

3. The method as defined in claim 2, wherein said composition containing an effective amount of laminarin is in liquid form.

4. The method as defined in claim 3, wherein said liquid composition containing an effective amount of laminarin contains 0.005 to 10% by weight of laminarin.

5. The method as defined in claim 3, wherein said composition containing an effective amount of laminarin also includes at least one additional substance selected from the group consisting of deficiency-correcting elements, fungicides, insecticides, herbicides, growth hormones, lipoamino acids and betaines.

6. A method for accelerating seed germination comprising a step of applying a composition containing an effective amount of laminarin to a seed.

7. The method as defined in claim 6, wherein said composition containing an effective amount of laminarin is applied to the seed by being added to the soil in which the seed is planted.

8. The method as defined in claim 7, wherein said composition containing an effective amount of laminarin is in solid form.

9. The method as defined in claim 7, wherein said composition containing an effective amount of laminarin is in liquid form.

10. The method as defined in claim 7, wherein said effective amount of laminarin is in the range of 1 g to 100 g/100 kg of seeds.

11. The method as defined in claim 7, comprising a preliminary step of determining the effective amount of laminarin that will accelerate the germination of the seed to which said composition is applied.

12. The method as defined in claim 6, wherein said composition containing an effective amount of laminarin is in solid form.

13. The method according to claim 12, wherein said composition contains from 0.005 to 50% by weight of laminarin.

14. The method as defined in claim 6, wherein said composition containing an effective amount of laminarin is in liquid form.

15. The method as defined in claim 14, wherein said composition containing an effective amount of laminarin is in the form of a film coating solution.

16. The method according to claim 14, wherein said composition contains from 0.005 to 50% by weight of laminarin.

17. The method as defined in claim 6, wherein said composition containing an effective amount of laminarin includes at least one additional substance selected from the group consisting of deficiency-correcting elements, fungicides, insecticides, herbicides, growth hormones, lipoamino acids and betaines.

18. The method as defined in claim 6, wherein said effective amount of laminarin in the range of 1 g to 100 g/100 kg of seeds.

19. The method as defined in claim 6, comprising a preliminary step of determining the effective amount of laminarin that will accelerate the germination of the seed to which said composition is applied.

* * * * *